United States Patent [19]

Schwab et al.

[11] 3,991,089
[45] Nov. 9, 1976

[54] BIS(METHYL n-OCTADECANOATE-9(10)-yl) SULFIDES AND METHODS, LUBRICANT COMPOSITIONS

[75] Inventors: Arthur W. Schwab; Lyle E. Gast, both of Peoria, Ill.

[73] Assignee: The United States of America as represented by the Secretary of Agriculture, Washington, D.C.

[22] Filed: July 14, 1975

[21] Appl. No.: 595,958

[52] U.S. Cl. .................. 260/410.9 R; 252/48.6; 252/433; 260/399; 260/481 R
[51] Int. Cl.² .................. C08H 3/00; C10M 1/38; C11C 3/02
[58] Field of Search ......... 260/399, 481 R, 410.9 R; 252/433, 48.6

[56] References Cited
UNITED STATES PATENTS 2,289,438  7/1942  Knowles et al. ............... 260/399
3,041,284  6/1962  Calhoun et al. ............... 260/399 X

OTHER PUBLICATIONS

Schwab, A. W. et al., "Hydrogen Sulfide Adducts of Methyl Oleate and Linoleate," J. Amer. Oil Chem. Soc. 50(9), pp. 364–366.

Primary Examiner—Helen M. McCarthy
Attorney, Agent, or Firm—M. Howard Silverstein; David G. McConnell

[57] ABSTRACT

Load-bearing lubrication compositions are prepared by adding to lubricating oil base stocks small amounts of sulfurized oleic alkyl esters or sulfurized alkyl esters of oleic acid-containing vegetable oils. A method of preparing the sulfurized fatty compounds is also disclosed.

6 Claims, 3 Drawing Figures

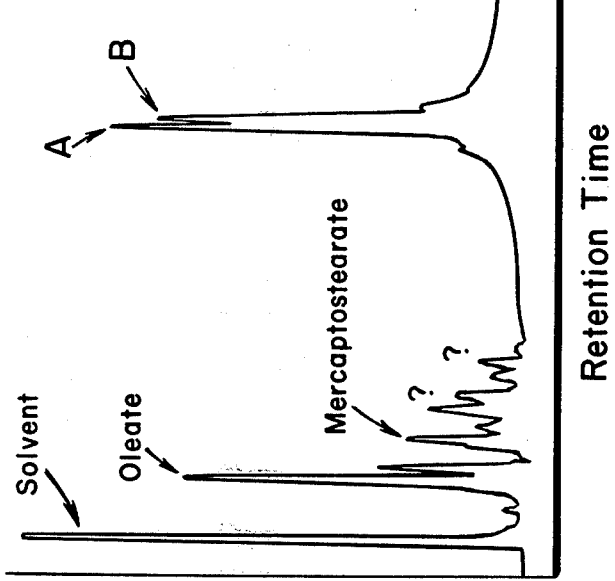
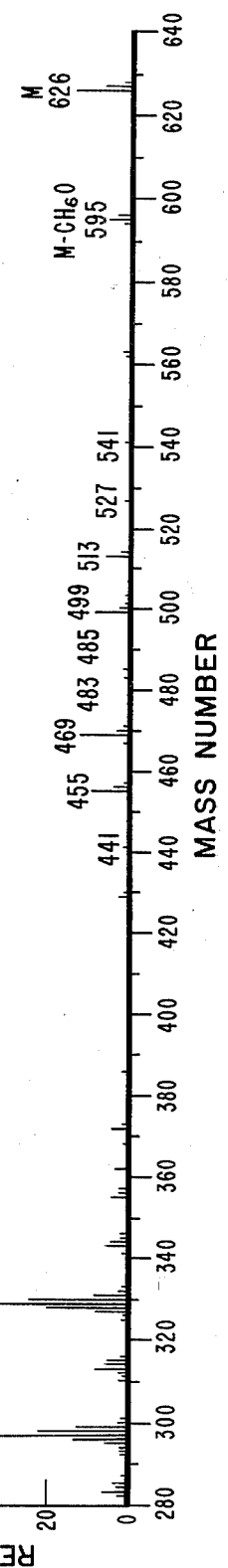

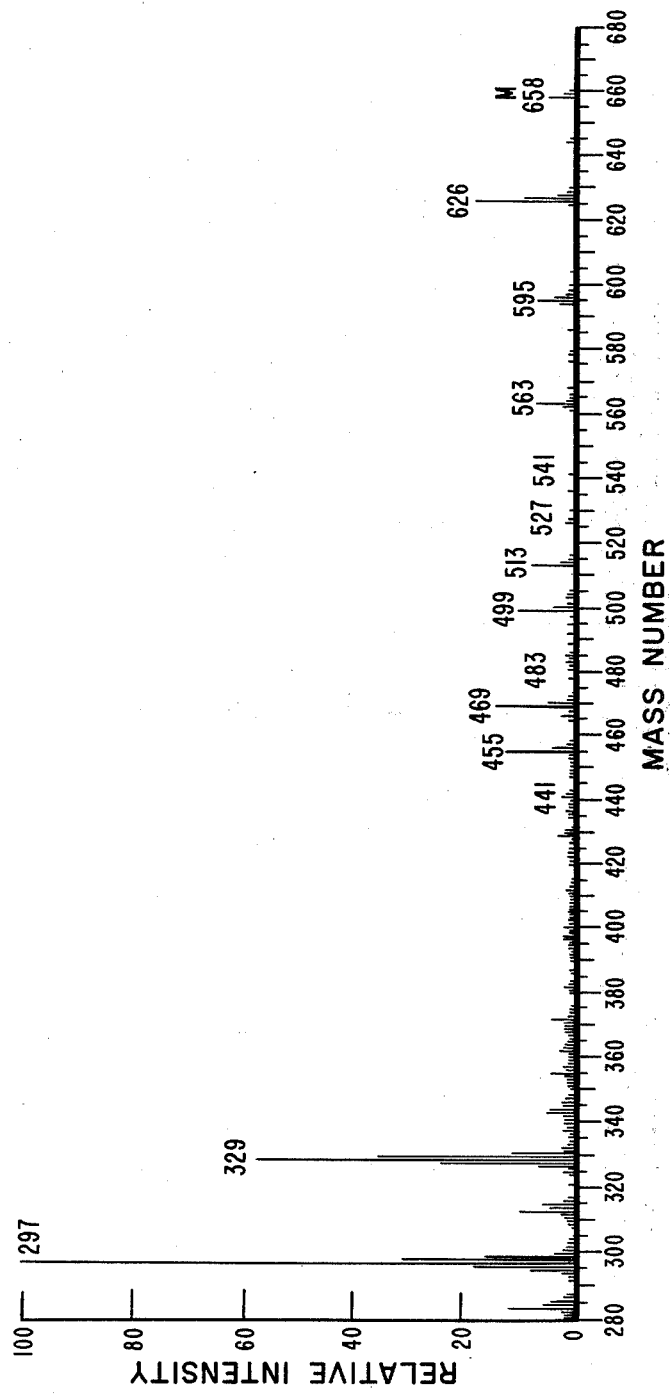

BIS(METHYL n-OCTADECANOATE-9(10)-yl) SULFIDES AND METHODS, LUBRICANT COMPOSITIONS

BACKGROUND OF THE INVENTION

This invention relates to lubricant compositions containing small amounts of sulfurized oleic alkyl esters or sulfurized alkyl esters of oleic acid-containing vegetable oils as load-bearing additives. It further relates to methods of preparing the additives.

There are generally two types of load-bearing lubricant additives, "antiwear" and "extreme pressure" (EP). When two lubricated surfaces are pressing against each other under a light load, they are separated from each other by a film of oil. As the load increases the film becomes thinner, and an antiwear additive is added to the lubricant to strengthen the film. However, under extreme pressure conditions the film strengthening properties of the antiwear additives become ineffective and the oil film collapses and the metal surfaces weld. EP additives contain components which prevent welding by reacting with the metal surfaces to form a coating of inorganic metal compounds.

Sulfurized sperm oil has long been recognized as an efficient EP additive for many lubrication oils. However, due to the fact that sperm whales are on the endangered species list, there has been much activity in the search for replacements for this desirable product. Sulfurized fatty oil and esters such as the synthetic esters of oleyl oleate and sulfurized lard oil are some of the compositions having EP properties which are similar to sulfurized sperm oil.

We have found a method for preparing sulfurized compounds suitable for use as extreme pressure lubricant additives from oleic alkyl esters and oleic acid-containing vegetable oils which comprises reacting one part of an oleic acid-containing vegetable oil dissolved in about 13 parts toluene or other suitable solvent which a stoichiometric excess of hydrogen sulfide at about $-20°$ C. in the presence of a catalytic amount of boron trifluoride.

DETAILED DESCRIPTION OF THE INVENTION

The drawings consist of the follwoing FIG. 1, a gas chromatogram of methyl oleate sulfurized in accordance with the invention; FIG. 2, a mass spectrograph of bis[methyl n-octadecanoate-9(10)-yl] sulfide; and FIG. 3, a mass spectrograph of a mixture of bis[methyl n-octadecanoate-9(10)-yl] sulfide and bis[methyl n-octadecanoate-9(10)-yl] disulfide.

We found that methyl oleate reacts with hydrogen sulfide in the presence of UV radiation to form methyl mercaptostearate and that methyl linoleate reacts under the same conditions to form approximately equal amounts of 9-(2-pentyl-l-thiolan-5-yl) nonanoate and 8-(2-hexyl-l-thiolan-5-yl) octanoate, herein defined as cyclic sulfides [Schwab et al., JAOCS 50(9): 364–366 (1973); and Schwab and Gast, JAOCS 47(10): 371–373 (1970)]. Soybean oil treated in the same manner results predominantly in the formation of mercapto and thiolan oils (Schwab et al., supra).

The reaction of methyl oleate with hydrogen sulfide in hexane at $-70°$ for 4 hours and $+25°$ C. for 7 hours results in the formation of 89% and 57% methyl mercaptostearate, respectively, when catalyzed by boron trifluoride. Methyl linoleate reacts with hydrogen sulfide under the same conditions to form a mixture of the cyclic sufides in yield of 83.8% and 64.5%, respectively. Temperature programmed gas-liquid chromatography (GLC) of the above reaction products reveals that essentially all components are eluted at temperatures below $250°$ C.

Soybean oil reacted with hydrogen sulfide in hexane at $-70°$ C. in the presence of boron trifluoride to form a mixture, which after being esterified to methyl esters, was analyzed by temperature programmed GLC. The mixture contained 27% methyl mercaptostearate, 52% of the cyclic sulfides and unreacted saturated fatty methyl esters. There were no components eluted above $250°$ C.

In view of the above we were surprised to find that soybean oil (SBO) dissolved in toluene at a SBO:toluene ratio of 1:13(i.e., an amount of toluene just sufficient to completely dissolve the SBO) reacted with a stoichiometric excess of hydrogen sulfide at a temperature of $-20°$ C. in the presence of boron trifluoride to form after esterification only 9.2% methyl mercaptostearate, 36% cyclic sulfides, 22.2% unreacted saturates, 23% side products, all of which eluted from the temperature programmed GLC below $250°$ C., and 9.4% of a substance which eluted at about $290°$ C. This substance proved to be bis[methyl n-octadecanoate-9(10)-yl] sulfide which has the following structure:

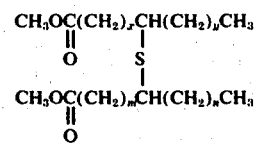

where $x$, $y$, $m$, and $n = 7$ or 8, and $x + y = 15$, $m + n = 15$. The requirement of toluene appears to be one of complete solubility of the vegetable oil at a temperature of $-20°$ C. Those skilled in the art will know of other solvents which are equivalent to toluene for the purpose of the invention.

We also found that equimolar amounts of methyl mercaptostearate and methyl oleate in toluene at about $25°$ C. in the presence of boron trifluoride react with hydrogen sulfide to form a mixture of bis[methyl n-octadecanoate-9(10)-yl] sulfide and bis[methyl n-octadecanoate-9(10)-yl] disulfide (see FIG. 1).

The disulfide has the following structure:

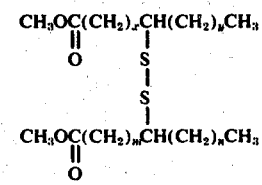

where $x$, $y$, $m$, and $n = 7$ or 8, and $x + y = 15$, $m, + n = 15$.

Although it is not completely understood, the producion of the bis-sulfides from soybean oil appears to result from the reaction of methyl mercaptostearate and the oleate fraction of the oil, the mercaptostearate being produced first by the reaction of hydrogen sulfide with the oleate fraction.

Oleic acid-containing vegetable oils are defined herein to mean those glyceride oils containing oleic acid as a major component of the glyceride structure.

This includes soybean oil, safflower oil, sunflower oil, olive oil, and cottonseed oil.

A stoichiometric excess of hydrogen sulfide is defined herein to mean any excess of the theoretical amount of hydrogen sulfide needed to react with all of the double bonds contained in the starting material. In the instance of the method of the invention, the toluene in which the soybean oil was dissolved was saturated with $H_2S$ prior to the start of reaction, and during the reaction, the $H_2S$ saturation was maintained by continuously bubbling the $H_2S$ gas through the reaction mixture.

The following examples are for the purpose of further illuminating the invention and are not to be construed as limiting the scope of the invention which is defined by the claims, infra. All parts and percentages disclosed herein are by weight unless otherwise specified.

EXAMPLE 1

Preparation of methyl mercaptostearate

A 100-ml. graduate with a Teflon-coated magnet was mounted in a propanol-dry ice bath inside a Dewar flask and the system cooled to −70° C. Hydrogen sulfide was introduced through a fritted glass sparger tube until approximately 20 ml. collected. The magnetic stirrer was started, and a 1-g. sample of methyl oleate dissolved in 20 ml. of hexane was added to the liquid hydrogen sulfide. Boron trifluoride was then introduced (at a rate of approximately one bubble per second) from a compressed gas cylinder. After 4 hours the boron trifluoride flow was stopped and the reaction mixture permitted to reach room temperature with stirring (usually stood overnight). After complete degassing a yellow oil remained. Diethyl ether (50 ml.) was added and the ether layer water-washed in a separatory funnel with 100 ml. of distilled water. The ether layer was separated and dried over anhydrous sodium sulfate. The ether was removed on the steam bath with nitrogen ebullition.

The reaction products were analyzed on a 7620 A Series Hewlett-Packard gas chromatograph having a 6 ft. × ¼ in. stainless steel column packed with 12.5 g. of 3% silicone rubber (JXR) on Gas-Chrom Q. Program runs were conducted at 180°–300° C. with a heating rate of 2°/minute and a helium carrier gas flow rate of 30cc./minute. The reaction product contained 2.4% methyl oleate, 88.9% methyl 9(10)-mercaptostearate, and 8.7% side products. The GLC instrument was fitted with a microsplitter-collector, which provided a 1:10 split ratio, one part to the flame ionization detector and 10 parts to a 2-in. No. 14 Teflon collector tube. Methyl mercaptostearate was collected and rechromatographed to increase purity.

EXAMPLE 2

Example 1 was repeated with methyl linoleate instead of methyl oleate. GLC showed the reaction product to be 0.9% methyl oleate, 83.3% of an approximately equimolar mixture of cyclic sulfides [i.e., methyl 9-(2-pentyl-1-thiolan-5-yl) nonanoate and methyl 8-(2-hexyl-1-thiolan-5-yl) octanoate], and 15.3% side products. The cyclic sulfide mixture was purified by GLC as in Example 1.

EXAMPLE 3

Reaction of soybean oil with hydrogen sulfide at −70° C.

Freshly deodorized, alkali-refined and bleached soybean oil (1 g.) was eacted with $H_2S$ and isolated in the same manner as described in Example 1. Approximately 0.15 g. of the reaction product was saponified with 4 ml. of 0.5 N methanolic sodium hydroxide and methylated with methanolic $BF_3$. The methyl esters analyzed by GLC in the manner described in Example 1 contained 10.0% methyl palmitate, 6.7% methyl stearate, 26.9% methyl 9(10)-mercaptostearate, 52.2% of cyclic sulfides, and 4.2% side products. The soybean oil starting material, methylated and analyzed by GLC as above, contained 10.3% methyl palmitate, 5.4% methyl stearate, 23.3% methyl oleate, 51.9% methyl linoleate, and 9.0% methyl linolenate.

EXAMPLE 4

Reaction of soybean oil with hydrogen sulfide at −20° C.

Ten grams of the soybean oil used in Example 3 were dissolved in 150 ml. of toluene and reacted at −20° C. with hydrogen sulfide in the manner described in Example 1. After 7 hours reaction, the reaction products were isolated, methylated, and analyzed by GLC as described in Example 1. The reaction product contained 12.3% methyl palmitate, 9.9% methyl stearate, 9.2% methyl 9(10)-mercaptostearate, 36.1% cyclic sulfide, 23.1% unidentified side products (all of which eluted at temperatures less than 250°), and 9.4% bis[methyl n-octadecanoate-9(10)-yl] sulfide which eluted at about 290° C.

EXAMPLE 5

One gram of methyl 9(10)-mercaptostearate prepared as described in Example 1 and 0.9 g. methyl oleate were dissolved in 10 ml. of toluene at 25° C. The mixture was stirred while $BF_3$ was bubbled through at one bubble per minute. These conditions were maintained for 16 hours, after which the reaction mixture was water washed, and the isolated reaction products were analyzed as described in Example 1. GLC analysis of the reaction product (FIG. 1) showed approximately 15% methyl oleate, 15% methyl 9(10)-mercaptostearate, 50% of an approximately equimolar mixture of bis[methyl n-octadecanoate-9(10)-yl] sulfide and bis[methyl n-octadecanoate-9(10)-yl] disulfide, and 20% side products.

The two bis-sulfide fractions were collected from the gas chromatograph as described in Example 1 and analyzed by mass spectroscopy.

Mass spectra were measured on a Nuclide 12-90 DF mass spectrometer equipped with a probe inlet; source temperature, 200° C., and 70 V electron energy.

FIG. 2 shows a mass spectrograph of GLC fraction A, FIG. 1, with a parent mass of 626 (i.e., a molecular weight of 626) and had fragmentation peaks at 595 due to loss of one methoxy and at 563 due to loss of two methoxy groups. Peaks at 513 and 499 are due to cleavage alpha to the sulfur branch and loss of the hydrocarbon end of the fatty acid, whereas peaks at 469 and 455 are due to a similar cleavage but loss of the ester end. Peaks at 329 and 297 are due to cleavage of the carbon sulfur bonds joining the two fatty esters.

FIG. 3 is a mass spectrograph of GLC fraction B, FIG. 1, and is identical with that of GLC fraction A except that the parent peak is at mass 658 (i.e., a molecular weight of 658), which corresponds to the addition of one sulfur atom.

EXAMPLE 6

The purified products of Examples 1 and 2, and the methyl esters of sulfurized soybean oil product of Example 4 were each dissolved at an addition level of 5% in white, heavy, domestic mineral oil having a Saybolt viscosity of 335/350. Control compositions were prepared which consisted of the mineral oil alone, mineral oil containing 5% sulfurized sperm oil (6% sulfur), and mineral oil containing 5% sulfurized lard oil. All of the above lubricant compositions were tested for wear preventative characteristics according to ASTM Method D2266-67 (reported as wear scars, mm.) and for extreme pressure properties according to ASTM Method D2596-69 (reported as weld point, kg.), Table 1.

Table 1

| Lubricant additive | Wear scars, mm. | Weld point, kg. |
| --- | --- | --- |
| Example 1 | 0.452 | 150 |
| Example 2 | 0.550 | 140 |
| Example 4 | 1.020 | 160 |
| Sulfurized sperm oil | 0.680 | 190 |
| Sulfurized lard oil | 0.650 | 175 |
| Mineral oil | 0.710 | 130 |

I claim:

1. A method of preparing bis[methyl n-octadecanoate-9(10)-yl] sulfide which comprises reacting one part oleic acid-containing vegetable oil dissolved in about 13 parts toluene with a stoichiometric excess of hydrogen sulfide at about −20° C. in the presence of a catalytic amount of boron trifluoride, isolating and methylating the reaction product.

2. A method as described in claim 1 wherein the vegetable oil is soybean oil, safflower oil, sunflower oil, or cottonseed oil.

3. A method of preparing bis[methyl n-octadecanoate-9(10)-yl] sulfide and bis[methyl n-octadecanoate-9(10)-yl] disulfide which comprises reacting methyl 9(10)-mercaptostearate with methyl oleate in equal molar amounts in toluene and in the presence of a catalytic amount of boron trifluoride.

4. The compound bis[methyl n-octadecanoate-9(10)-yl] sulfide having the following structure:

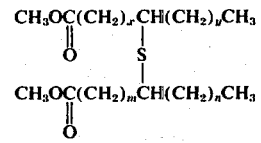

where $x$, $y$, $m$, and $n = 7$ or 8, and $x + y = 15$, $m + n = 15$; said compound being characterized by the mass spectrograph of FIG. 2 and a molecular weight of 626.

5. The compond bis[methyl n-octadecanoate-9(10)-yl] disulfide having the following structure:

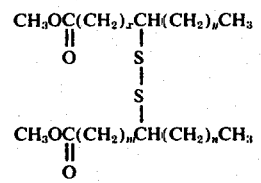

where $x$, $y$, $m$, and $n = 7$ or 8, and $x + y = 15$, $m + n = 15$; said compound being characterized by the mass spectrograph of FIG. 3 and a molecular weight of 658.

6. A composition comprising a mixture of bis[methyl n-octadecanoate-9(10)-yl] sulfide and bis[methyl n-octadecanoate-9(10)-yl] disulfide.

* * * * *